(12) United States Patent
Robitaille et al.

(10) Patent No.: US 9,103,812 B2
(45) Date of Patent: Aug. 11, 2015

(54) PHOTO-COUPLED DATA ACQUISITION SYSTEM AND METHOD

(75) Inventors: Valérie Robitaille, Québec (CA); Cody Andrews, Québec (CA)

(73) Assignee: XPERTSEA SOLUTIONS INC., Quebec (CA)

(*) Notice: Subject to any disclaimer, the term of this patent is extended or adjusted under 35 U.S.C. 154(b) by 0 days.

(21) Appl. No.: 13/994,618

(22) PCT Filed: Dec. 22, 2011

(86) PCT No.: PCT/CA2011/050800
§ 371 (c)(1),
(2), (4) Date: Jun. 14, 2013

(87) PCT Pub. No.: WO2012/083461
PCT Pub. Date: Jun. 28, 2012

(65) Prior Publication Data
US 2013/0273599 A1    Oct. 17, 2013

Related U.S. Application Data

(60) Provisional application No. 61/426,636, filed on Dec. 23, 2010.

(51) Int. Cl.
| | |
|---|---|
| *G01N 21/00* | (2006.01) |
| *G01N 33/18* | (2006.01) |
| *A01K 61/00* | (2006.01) |
| *A22C 29/00* | (2006.01) |
| *G01N 21/51* | (2006.01) |
| *G01N 21/55* | (2014.01) |

(Continued)

(52) U.S. Cl.
CPC ............. *G01N 33/18* (2013.01); *A01K 61/00* (2013.01); *A01K 61/001* (2013.01);
(Continued)

(58) Field of Classification Search
CPC ............ G01N 27/223; G01N 27/3273; G01N 21/658; G01N 27/3271; G01N 33/54373; G01N 2021/3144; G01N 21/49; G01N 27/413; G01N 27/44791; G01N 33/5008; G01N 33/5438; G01N 33/554; G01N 2035/00158
See application file for complete search history.

(56) References Cited

U.S. PATENT DOCUMENTS 5,133,145 A * 7/1992 McDonald ...................... 43/17.5
5,474,030 A * 12/1995 Pittet et al. ...................... 119/207
(Continued)

FOREIGN PATENT DOCUMENTS

WO   WO/2006/017141   2/2006
WO   WO/2010/059176   5/2010

OTHER PUBLICATIONS

International Search Report issued for PCT/CA2011/050800, dated Mar. 13, 2012, 3 pages.

*Primary Examiner* — Michael P Stafira
(74) *Attorney, Agent, or Firm* — Norton Rose Fulbright US LLP

(57) ABSTRACT

The photo-coupled data acquisition system can have a container having a contour wall extending upwardly from a closed bottom, for containing a sample therein, a light emitter operable to emit diffused light into the container at an initial intensity, a photodetector operable to detect a reflected intensity of the diffused light, and a structure connected to the contour wall and holding the light emitter and the photodetector at a predetermined height above the bottom of the container and in an orientation facing inside the container, wherein during operation of the system, the initial light intensity is attenuated by the sample and the reflected intensity thereof can be correlated to an information value concerning a variable of interest of the sample.

11 Claims, 5 Drawing Sheets

(51) Int. Cl.
*G06M 11/00* (2006.01)
*G06M 1/10* (2006.01)

(52) U.S. Cl.
CPC ............ *A01K 61/005* (2013.01); *A22C 29/005* (2013.01); *G01N 21/51* (2013.01); *G01N 21/55* (2013.01); *G06M 1/101* (2013.01); *G06M 11/00* (2013.01); *G01N 2201/0212* (2013.01); *G01N 2201/065* (2013.01); *G01N 2201/0627* (2013.01)

(56) References Cited

U.S. PATENT DOCUMENTS

| | | | |
|---|---|---|---|
| 8,173,438 B1* | 5/2012 | Putnam et al. | 436/138 |
| 2002/0089669 A1* | 7/2002 | Liu et al. | 356/436 |
| 2010/0072371 A1* | 3/2010 | Wagner | 250/343 |
| 2011/0160073 A1* | 6/2011 | Kordunsky et al. | 506/9 |
| 2012/0105837 A1* | 5/2012 | Ingber | 356/246 |

* cited by examiner

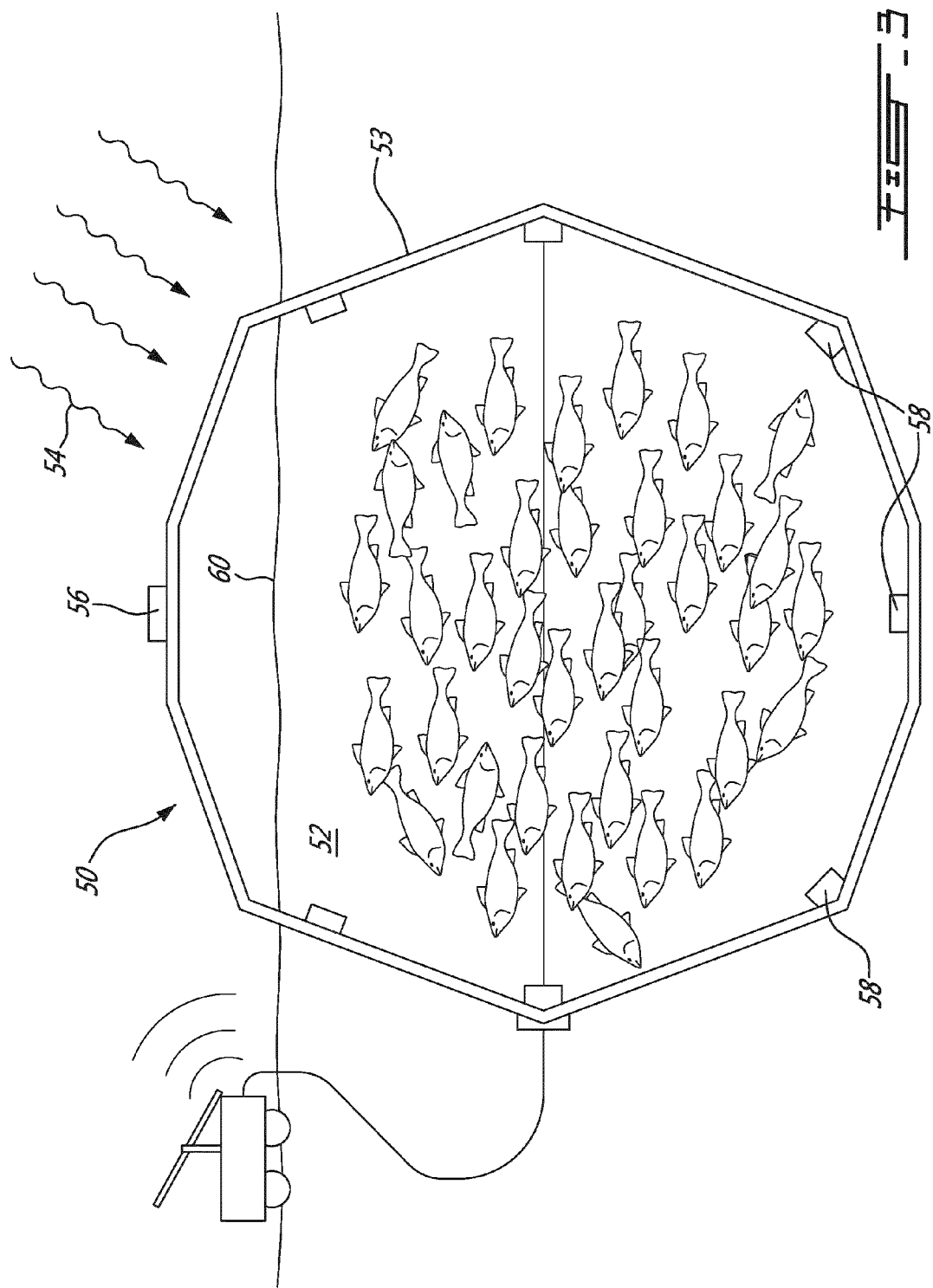

PHOTO-COUPLED DATA ACQUISITION SYSTEM AND METHOD

FIELD

This specification concerns systems and methods which use photodetection of a light signal attenuated by a sample to determine a value of a variable of interest of concerning the sample. For example, in one embodiment, the attenuation of light as it travels across a sample having organisms in a water medium affects the detected intensity, which can thus be correlated to a value of a variable of interest such as an quantity, biomass, or activity level of the organisms, for instance.

SUMMARY

In accordance with one aspect, there is provided a photo-coupled data acquisition system comprising a container having a contour wall extending upwardly from a closed bottom, for containing a sample therein, a light emitter operable to emit diffused light into the container at an initial intensity, a photodetector operable to detect a reflected intensity of the diffused light reflected by at least one of the sample and the container across the sample, and a structure connected to the contour wall and holding the light emitter and the photodetector at a predetermined height above the bottom of the container and in an orientation facing inside the container, wherein during operation of the system, the initial light intensity is attenuated by the sample in a manner that the reflected intensity can be correlated to an information value concerning a variable of interest of the sample.

In accordance with another aspect, there is provided a method of obtaining a value of a variable of interest concerning a sample of organisms in a liquid medium, the method comprising: placing a given volume of the sample in a container; emitting an initial intensity of diffused light onto the sample, the container receiving the diffused light and reflecting the diffused light through the sample, the sample thereby attenuating the initial intensity; measuring a reflected intensity of the diffused light; and correlating the measured reflected intensity to the variable of interest.

In accordance with another aspect, there is provided a method of obtaining an information value concerning a variable of interest of a sample having marine organisms in a water medium, the method comprising: exposing the sample having marine organisms in a water medium to a diffused light having an initial intensity, the sample thereby attenuating the light; obtaining at least one attenuated intensity value corresponding to an attenuated intensity of the light subsequently to said exposing; using the at least one attenuated intensity value to obtain the information value of the sample.

Wherein the variable of interest can be related to the biomass of the marine organisms in the sample, in which case said using includes correlating the at least one attenuated intensity value to a biomass of the marine organisms.

Wherein the step of using can include obtaining an initial intensity value corresponding to the initial intensity, determining an attenuation value using both the attenuated intensity value and the initial intensity value, providing calibration data, and correlating the attenuation value to the information value of the variable of interest using the calibration data.

Wherein the calibration data can be based on a calibration curve obtained using a plurality of samples of having known and varying variables of interest yielding a corresponding plurality of attenuation factors.

Wherein said exposing can include emitting diffused light onto the sample.

Wherein an intensity value of ambient light can be obtained and the attenuated intensity values can be corrected based on the measured ambient light intensity value.

Wherein the at least one attenuated intensity values can be obtained for two distinct wavelength bands, in which case the step of using can include using at least one attenuated intensity value obtained for one of the two distinct wavelength bands to obtain the information value corresponding to a first variable of interest; an attenuated intensity ratio of corresponding values in the two distinct wavelength bands can be correlated to obtain an information value corresponding to a second variable of interest; and the exposing includes emitting diffused light onto the sample at initial intensities in the two distinct emission wavelength bands.

Wherein the diffused light can be sunlight, in which case an initial intensity value is determined by measuring an ambient light intensity value, and the initial intensity value can be used to obtain the information value.

Wherein the at least one attenuated intensity value can be obtained by detecting a reflected intensity of the light.

Wherein the at least one attenuated intensity value can be obtained by detecting a transmitted intensity of the light.

Wherein the at least one attenuated intensity value can include a plurality of attenuated intensity values obtained at a regular rate over a given period of time, in which case the plurality of attenuated intensity values can be analyzed to determine at least one frequency of variation of the plurality of attenuated intensity values during the given period of time, and the at least one frequency can include at least two frequencies corresponding to two respective variables of interest of the sample.

Wherein the obtaining can include obtaining at least two attenuated intensity values corresponding to an attenuated intensity of the light subsequently to said exposing, said at least two attenuated intensity values being obtained for different field of views, in which case the at least two attenuated intensity values can be compared and an indication of the size of the marine organisms can be obtained using said comparison.

One specific need occurred in the field of post-larvae shrimp production. In the shrimp industry, post-larvae shrimp are produced before being shipped to shrimp farms. The shrimp farms typically pay a price for the post-larvae shrimp which depends on the quantity of post-larvae shrimp. There are very large numbers of post-larvae shrimp to count, and there remained a need for improved means to obtain at least a satisfactory estimate of the number of post-larvae shrimp for this purpose. There was thus a need for improved methods or systems for obtaining information concerning the biomass of marine organisms in a liquid medium.

In accordance with one aspect, there is provided a method of counting shrimp at the post-larvae stage of development, the method comprising: placing a sample of a given volume having the shrimp at the post-larvae stage in a water medium in an opaque container; emitting an initial intensity of diffused light onto the sample; measuring a reflected intensity of the light; correlating the measured reflected light intensity to an estimated number of shrimp, thereby counting the shrimp.

In accordance with still another aspect, there is provided a system for counting shrimp, the system comprising a container for housing a predetermined volume of a sample containing the shrimp in a water medium, the container further being opaque and preventing intrusion of ambient light, a diffused light emitter for emitting an initial light intensity toward the sample in the container, and a photodetector for detecting a reflected light intensity, the diffused light emitter and photodetector being held at a predetermined height above the sample, and a processor to correlate the reflected light intensity to a number of shrimp in the water medium.

An other specific need occurred in the field of fish farms, particularly in open sea cages. One of the most major costs in fish production is the cost of the feed. The ratio of the amount of feed per pound of fish produced is thus an important factor in successful fish production, and it is thus desirable to reduce the amount of feed used. Particularly in open sea cages, it was difficult to efficiently and precisely determine at which moment to stop providing feed to the fish. It was common to feed the fish with too much feed, and the excess amount of feed settled across the open sea cage and past it, to be lost. There thus remained a need for improved means to determine when to stop providing feed to open sea cages.

In accordance with another aspect, there is provided a method of determining when to stop providing feed to a sample of fish swimming in sea water and contained in an open sea cage, the method comprising: transmitting a diffused light having an initial intensity across the sample, the sample thereby attenuating the light; measuring plurality of attenuated intensity values of the transmitted light, the attenuated intensity values being obtained at a regular rate over a given period of time; identifying a first frequency of variation of the plurality of attenuated intensity values over the period of time corresponding to the movement of the fish; identifying a second frequency of variation of the plurality of attenuated intensity values over the period of time corresponding to the movement of feed; and determining when to stop providing feed based on a variation of the attenuated intensity values corresponding to the second frequency.

Wherein diffused light can be emitted and transmitted through the sample within a given chromatic wavelength band, and the step of measuring can include measuring the attenuated intensity values within a corresponding chromatic wavelength band.

Wherein an ambient light intensity value can be measured within the corresponding chromatic wavelength band, and the attenuated intensity values can be corrected based on the measured ambient light intensity value.

Another specific need occurring in the field of open sea cages is the ultimate goal of fish farmers to achieve optimal fish growth while minimizing the consumption of expensive fish feed. Achieving the lowest feed conversion ratio requires that the farmer has a good estimate of the total biomass of fish present in the ocean aquaculture cage. Knowing the total fish biomass also enables the fish farm managers to perform accurate financial predictions related to fish stock, diminishing investment risks into the organization. It was common for fish farms to lose count of their fish stock after several months due to the lack of initial fish count assessment or high mortalities due to diseases or other environmental factors. There thus remained a need for improved means to determine the total fish biomass in open sea cages.

In accordance with another aspect there is provided a method of determining the biomass of fish including the number and the size of fish contained in an open sea cage, the method comprising: transmitting a diffused light having an initial intensity across the sample, the sample thereby attenuating the light; measuring plurality of attenuated intensity values of the transmitted light, the attenuated intensity values being obtained at a regular rate over a given period of time; identifying a first frequency of variation of the plurality of attenuated intensity values over the period of time corresponding to smaller fish; identifying a second frequency of variation of the plurality of attenuated intensity values over the period of time corresponding to larger fish; and correlating the total attenuation values corresponding to larger fish to a fish number and the total attenuation values corresponding to smaller fish to a fish number and solving for the total number of fish in the cage.

Wherein more than two sampling frequencies can be used to assess the fish population size distribution Wherein calibration algorithms that correlate attenuations values specific to the system to units of fish biomass for different fish species can be developed.

Wherein an ambient light intensity value within the corresponding chromatic wavelength band can be measured, and the attenuated intensity values can be corrected based on the measured ambient light intensity value.

Wherein water turbidity value can be measured within the corresponding chromatic wavelength band, and the attenuated intensity values be corrected based on the measured turbidity value.

Many further features and combinations thereof concerning the present improvements will appear to those skilled in the art following a reading of the instant disclosure.

DESCRIPTION OF THE FIGURES

In the figures,

FIG. 3 is a view showing a second embodiment of the system arranged on an open sea cage;

DETAILED DESCRIPTION

Figure 1:
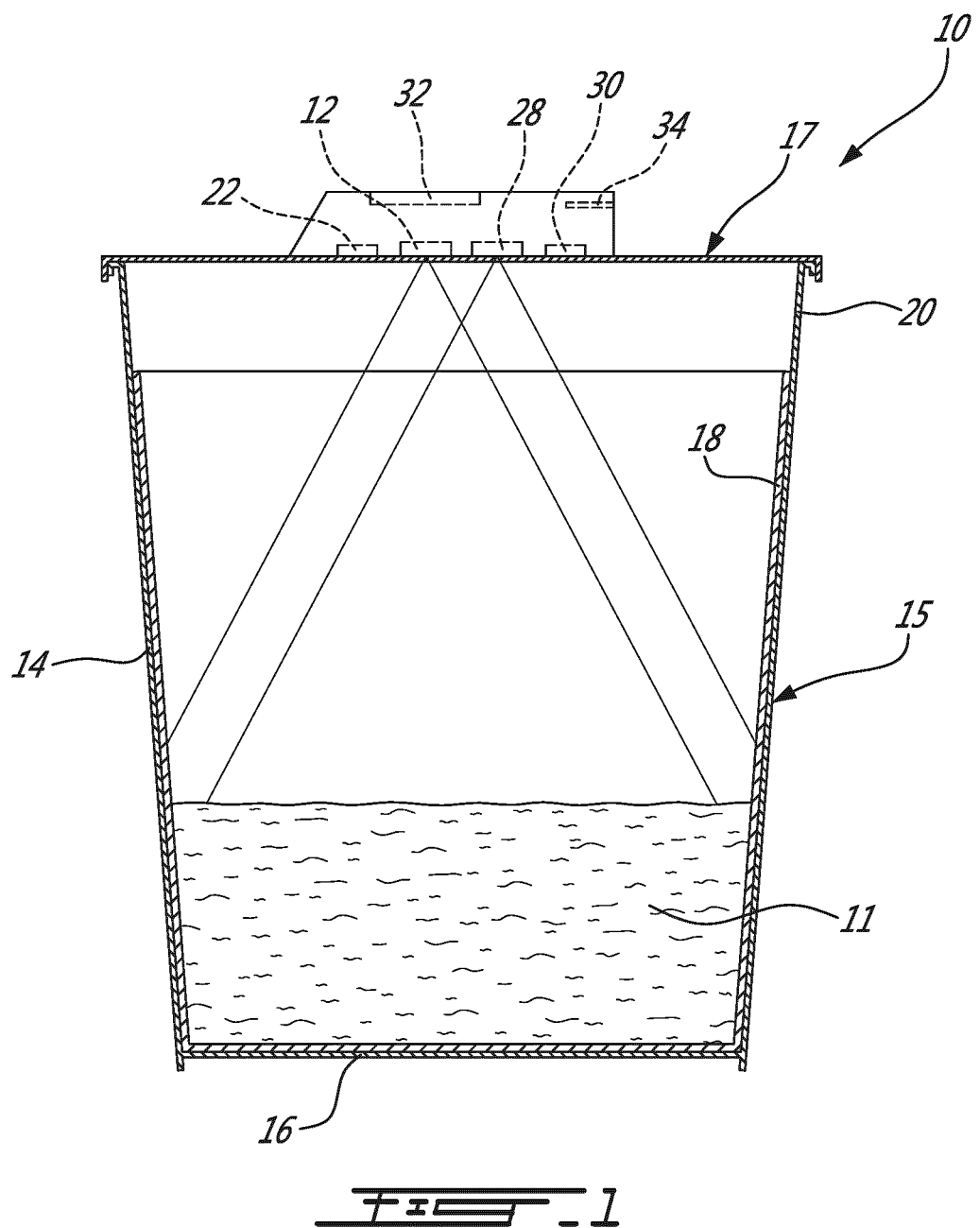
FIG. 1 is a view of a system for counting shrimps in accordance with a first embodiment.

FIG. 1 shows an example of a photo-coupled data acquisition system 10 which can be used for obtaining information on a sample 11 which can have small marine organisms in a liquid medium for instance. In this particular example, the marine organisms can be shrimp, such as shrimps at the post-larvae stage or *Nauplii*, lobster larvae, sturgeon eggs, young mussels, micro algae, *Artemia*, in a water medium, to name a few examples, whereas information can be the biomass thereof. In cases where the size of the organisms is known and relatively constant, the biomass can be directly equated to a quantity of the organisms. Henceforth, the system 10 can be used for obtaining at least an estimation of the quantity of marine organisms in a water medium, prior to shipping for instance.

In FIG. 1, the system 10 has a container 15 which can receive a given volume of a sample 11 of the organisms in the liquid medium. In this example, the given volume is large compared to the size of the organisms so that there are a large amount of organisms in the sample. This can statistically allow to correlate the attenuation caused by the organisms in the container 15 to their biomass.

The system 10 can be seen to generally include an emitter 12 (light source) which can emit a diffused light onto the sample 11 at an initial intensity. The sample 11 attenuates the intensity of the light by scattering or absorbing the light, for instance. In this particular example, the attenuation of the signal will be a function of the biomass of shrimp in the sample 11 and can also be a function of the turbidity of the water medium and/or volume of the sample, to name possible variables. The quality of the signal can be affected by ambient light, and so the sample is placed in an opaque container, which can be covered by a removable opaque cover or lid 17 which both serves to form a closed volume with the container 15 to prevent intrusion of ambient light and to form a structure which holds the emitter 12 at a predetermined position (orientation and height) relative to the sample 11 for the light exposure configuration to be constant from one measure to another.

The container 15 has a contour wall 14 extending upwardly from a bottom 16. The inner face of the contour wall and of the bottom is reflective in this embodiment, in the sense that it can reflect the light emitted by the emitter 12 in a satisfactory manner. If reflection in more than one wavelength band is desired, or for simplicity, a white or mirror inner face can be selected. In the illustrated embodiment the combination of opacity and reflectivity characteristics are obtained by housing a white bucket 18 inside an opaque bucket 20 for example. A comparable effect can be achieved using a sufficiently thick white bucket and/or by painting or otherwise covering the inner face of the container with a white or reflective layer, for instance.

The system 10 can also be seen to generally include a photodetector 22. The photodetector 22 can obtain a measure indicative of the intensity of the attenuated signal which is reflected back. The photodetector can use an amplified silicon photodiode for instance which can allow to convert light intensity into voltage. It can be used in combination with a CCD lens for adaptability to distance and size of samples investigated.

The photo detector 22 is also held at a predetermined position (orientation and height) relative to the sample 11, by a structure formed by the lid 17, for the light exposure and detection configuration to be constant from one measure to another.

The use of a lid mounting locks the horizontal position (height) and orientation of the emitter 12 and photodetector 22 relative the sample 11. However, the radial orientation at which the lid 17 is secured relative to the container 15 is one possible source of lack of constancy in the light exposure from one measure to another. However, if the container 15 is symmetrical around the axis of the lid 17, including the reflectivity characteristics of the inner wall, such as in the cylindrical shape shown in FIG. 1, the effects of the relative orientation of the lid 17 relative the container 15 can be negligible since the measure would likely be the same at any radial orientation. In any event, means such as mechanical locks or indications can be used to assist the user in positioning the lid 15 repeatedly in the correct position if desired, or the emitter 12 and detector 22 can be positioned close to the center of the lid to minimize undesirable effects of variations in radial orientation, for instance.

A horizontal marking, for instance, can be provided on the inner face of the contour wall 14 to provide an indication assisting the user in selecting the correct level of the sample 11 and thus providing a constant volume of the sample 11 in the system, if useful in view of the intended application of the specific embodiment.

Since the conditions of the measures can be made constant as discussed above, a biomass calibration curve of the system 10 can be obtained by testing a plurality of samples each having a different biomass of organisms of a known type, quantity and maturity, but maintaining all other parameters constant (such as volume of the sample and turbidity of the water medium). The detector 22 will obtain an intensity reading which will vary depending on the known organism quantity/biomass, which allows to draw the biomass calibration curve. Experiments have shown that the calibration curve can often be closely reproduced with a mathematical formulae in which the intensity is simply a variable, for instance. An empirical correlation table can alternately be used, for instance.

Once the biomass calibration curve has been obtained, using the system with the same sample volume and same water medium turbidity will yield a given intensity from which an unknown quantity of a given type and maturity of organism can be deducted using the calibration curve. Since many organisms can be characterized as having an average mass which varies from individual to individual within a limited extent, the biomass deducted can be equated to an estimated number of individuals. The intensity measurement can be taken in a specific spectral band, in the visible spectrum or any other satisfactory portion of the spectrum, or more generally with a broader spectrum such as white light, for instance.

One variable which may reduce the accuracy of the measures is the variance in the turbidity of the liquid medium. One way to correct future readings as a function of the turbidity is to first take a measure of a sample having only the liquid medium, i.e. without organisms. The attenuation will be affected by the turbidity and so the detected intensity will include an indication of the turbidity level. Knowing the turbidity level, the system can be calibrated to select the correct calibration curve, i.e. the calibration curve corresponding to the actual turbidity level.

The system can also include further features to be specifically adapted to obtain other information about the sample, such as turbidity of the water medium for instance. Similarly to that which is described above, a turbidity calibration curve can be obtained by using the system with a plurality of samples each having a different turbidity of the water medium, but other parameters being constant. In the specific example shown in FIG. 1, for instance, the system has two separate emitter 12, 28 and detector 22, 30 pairs, each corresponding to distinct wavelength bands. More accurate results can be obtained by using wavelengths which react more specifically to the organisms, or the medium in the sample 11. For instance the wavelengths of red and blue will react differently in the water medium and can be used to obtain satisfactory results. Alternately, green and blue was found to be a good combination to distinguish attenuation from organic and non-organic sources. This can be achieved with appropriately selected LEDs and appropriately selected detectors, optionally with filters, for instance. Typical LEDs can emit in a wavelength band on the order of 20 to 40 nm, whereas filters can be used to filter frequencies which are not in a band of the order of 10 to 20 nm, for instance. Alternately, in embodiments where energy consumption is less of an issue, lasers with diffusing lenses can be used instead. From the above, it will be understood that in alternate embodiments, the system can be adapted to obtain information concerning a variable concerning an inorganic source, such as sediments, in a liquid medium, for instance.

A three dimensional calibration curve (surface), or double correlation table set, can be obtained by using the system with a plurality of different amounts of shrimp, for each of a plurality of different turbidity levels. This curve can be accessed by using two different intensity data, such as intensity of reflected red and ratio of red and blue reflected intensities, for instance, to obtain information on the biomass of a sample having a water medium of unknown turbidity level. Taking the turbidity level of the water medium into consideration, or other influential variables, can help providing a better accuracy of the biomass estimation. In alternate embodiments, other wavelengths can be used. In alternate embodiments, a separate turbidity sensor can be used to obtain a turbidity reading and thereafter address the correct calibration curve, for instance. It will also be noted here that the use of two wavelengths can also provide other uses than determining the turbidity of water, such as determining an ratio of live feed relative to fish for instance, or determining the presence of parasites for instance.

In the specific embodiment described in FIG. 1, the system has two LED lights of different spectral emission band (blue and green) and two detection units, all installed through the tank lid 17. The detection units can be made of a photodiode and a driver circuit to optimize noise reduction and signal stability. The LED lights illuminate the tank uniformly through diffusing lenses. Since the tank is opaque and substantially light-hermetic, the illumination comes virtually exclusively from the LED sources. The detecting units each have a bandpass filter corresponding to the spectral emission of one of the LED. Light energy returned by the tank bottom that passes through the bandpass filter is converted into a voltage which is then recorded by a basic datalogger system. To keep the output power of the LED constant a fan unit can be installed to cool down the system. A datalogger unit can transmits the voltage intensity data for direct processing by an optional internal processor 32 or by an external computer connected via a port (not shown), for instance, or to a memory card 34 in an optional memory card port for instance, for subsequent access.

The tank lid 17 can be removed to add water and marine organisms into the tank/container 15 for counting. These operations can also be done through a trap on the cover, or on the side of the container, for instance. The lid is thus optional. Optionally, a mirror can be used on the bottom and/or wall of the bucket to increase the amount of reflected light which passes twice across the sample, and thereby improve accuracy, for instance.

Figure 2:
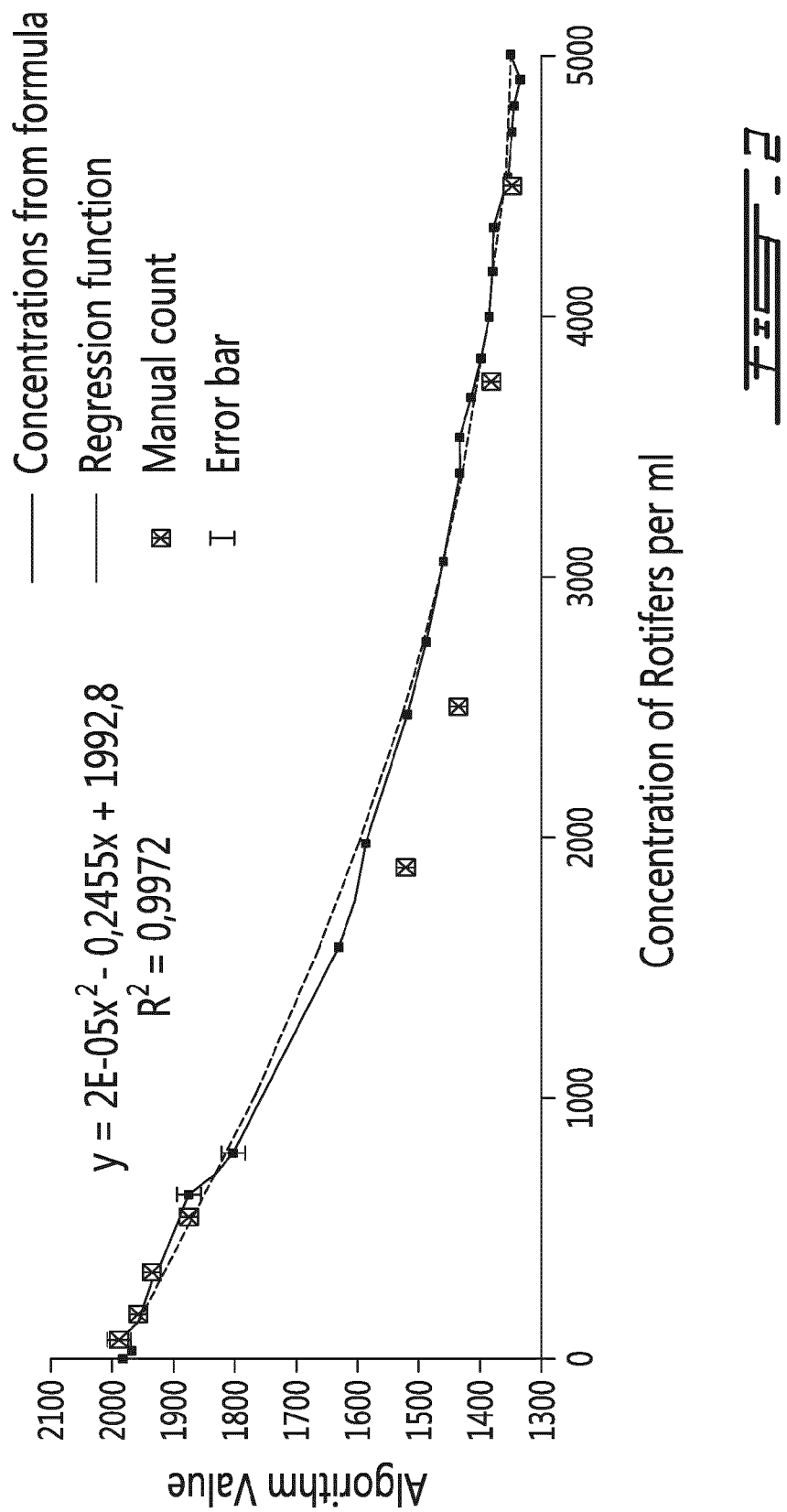
FIG. 2 is a graph showing a correlation between attenuated intensity and amount of rotifers per ml.

It will be understood that the system can be used to obtain information on various types of organisms or particulate matter, and it will be specifically noted that the system can be particularly adapted for obtaining information on the biomass of shrimp, live feed, such as *artemia* and rotifers, fish larvae, and shellfish larvae for instance, or even smaller organisms such as blood cells for instance in which case the system can be scaled to a smaller size. For example, FIG. 2 provides an example of a calibration curve which allows to roughly equate the attenuated intensity to an amount of rotifers per ml. Inorganic or organic particulate matter can also be characterized in a manner similar as that described above for characterizing turbidity, for instance.

Finally, it will also be understood that the system can also be scaled to larger sizes, and an alternate embodiment can be specifically adapted for land-based aquaculture in a reservoir which can contain large biomasses of fish in thousands of liters of water medium, or open sea cage applications, for instance. In embodiments where the sample cannot be shielded from ambient light, an ambient light detector and/or a filter arrangement can be used to help discern the influence of the ambient light from the useful intensity measurement.

Another example of information which can be obtained is the size of marine organisms, or other relevant variables of interest, using field of view ratios. A particle forward scattering phase function (FSPF) varies in function of the size of the particle; the bigger the particle the more it will reflect light in the forward direction. Smaller particles tend to distribute light uniformly in all directions. Therefore by recording information about the FSPF, it is possible to obtain information about the size of the particles in the water. Different fields of views can be obtained using two or more detectors each having for instance a CCD lens which can be adjusted to measure the intensity of reflected light at two or more corresponding fields of views. The FSPH of particles can be obtained by recording the ratio of reflectance between the light intensity recorded at narrow fields of views (ex. 10 degrees) and at large fields of views (ex. 20 degrees). Since marine organisms are free floating in a body of water, they behave like particles and this ratio of narrow to wide field of view can be correlated to an average size of the marine organisms present in the water tank. If more than two fields of views are used, it is possible to provide a size distribution function of the marine organisms. Using this technique one can generate as many size categories as there are fields of view ratios available.

The method used for the development of algorithms can link data concerning light measurements recorded by the system to the variables of interest (VOI) such as the number or size of organisms in the water or concentrations thereof. Two levels of algorithms can be used, including the calibration algorithms for external variables, and the processing algorithms to convert recorded data into meaningful information.

First, a standardization of the resulting light measurements for geometric and radiometric external variables of the system can be used. In fact, factors like the internal temperature of the system or humidity level can influence the output power of the laser or LED sources and impact light measurements. To maximize the accuracy of the processing algorithms, the influence of these external variables must be removed.

Calibration curves for external variables can be generated in laboratory then algorithms are developed and integrated into a computer program. This program automatically corrects the effects of the external variables on light reflectance measurements recorded by the system. For aquaculture applications, correction algorithms can be generated for the following external variables: light beam divergence; the distance between the light sources and the investigated specimens/sample, the internal temperature of the system, the humidity level, the water level, the optical properties (turbidity) of the water.

For each variable, an experiment can be conducted to assess its influence on the light reflectance measurements recorded by the system. The experiments can consist of measuring the reflectance of a white calibration target under different conditions specific to the external variable investigated. Correction algorithms are generated for the external variables that affect the light reflectance measurements by an order of magnitude equal to or higher than the accuracy of the system.

Similar to the previous external variable calibration process, laboratory experiments are conceived to establish correlations between the corrected reflectance measurements recorded by the system and the VOIs. During this second level of algorithm development, a function for each VOI is characterized. For example, the increase in live feed concentration may linearly decrease the light intensity measurements whereas the relationship between reflectance and a number of halibut larvae may be exponential.

Turning now to FIG. 3, another embodiment of a system 50 which can be used for obtaining information on a sample 52 of marine organisms in a water medium. In this particular example, the marine organisms are fish and the water medium is a volume of water present in an open ocean cage 53. The open sea cage is permeable to water so water flows through it as the volume remains relatively constant.

In this particular example, the emitter can be entirely omitted and the system can function based only on ambient light 54 (sunlight), for instance. More particularly, an ambient light detector 56 (which can be a pyrometer optionally with adapted filters) is positioned on top of the open ocean cage 53, and is oriented toward the sky. Its field of view should be wide enough so that it can remain substantially unaffected by the punctual presence of a cloud directly above it, for instance. The sunlight is transmitted into and across the sample 52 as it becomes attenuated. At least one detector 58 is provided under the water surface 60 in a path of the light which is affected by the presence of the fish. The reading of the attenuated light intensity detector 58 will be lower than the reading of the initial ambient light intensity because of the attenuation which takes place during transmission across the sample. The attenuated light intensity is a factor of the ambient light intensity (sunlight intensity), the biomass of fish in the cage, and the turbidity of the water medium. The ambient light intensity factor can be removed from the equation by knowing the initial intensity value, which can be achieved with the ambient light. Knowing the turbidity level can allow to remove the turbidity factor from the equation. Then, the attenuated light intensity measured by the detector(s) 58 can be used to obtain an indication of the biomass by using a previously obtained calibration curve. Determining the biomass of fish in the cage in real time can be particularly useful in obtaining an indication of the approximate amount of feed which should be provided.

Generally, using a greater number of detectors can allow improving the accuracy of the system and can also allow to access more information. For instance, the turbidity of the water can be detected by using a detector which is underwater, but which is in a path of the sunlight which is substantially out from interference from the interaction with the fish. Once the factor of initial light intensity is taken out of the equation using the information obtained using the ambient light sensor, the detected intensity can be directly linked to turbidity using an appropriate calibration curve, and the reading from a detector at the bottom of the cage can then be correlated to a biomass of fish in the cage.

One specific use which can be particularly advantageous is to assist in determining the right moment to stop providing feed to fish in the open sea cages. One way to achieve this in a manner potentially more efficient than by simply analysing data from one or more detectors at a given point in time, can include obtaining data from one or more detectors at a regular rate over a given period of time. For instance, readings can be obtained at a rate in the order of a twenty intensity measures per second. When feeding, the fish will move at a given average speed. The effect of the movement of the fish on the intensity measures will be that the intensity measures will fluctuate at a given rate. By analysing the readings, one can identify the frequency of variations in the intensity signal corresponding to the movement of the fish. Once the fish are satisfied, they will tend to remain at the surface of the water for a given period of time and continue to move at a given rate, but they will no longer consume all of the feed. Typical feeding pellets can sink at a rate in the order of 4 inches per second. Upon approaching the detector(s), the sinking pellets will create intensity fluctuations at a frequency peak which will be significantly different from the frequency peak due to the fish movement. Analysing the intensity variation spectrum can allow to detect the occurrence of the frequency peak associated with the occurrence of sinking pellets. The system can be programmed so that a user is alerted to slow, or stop conveying the feed once predetermined thresholds of the frequency peak associated with the occurrence of sinking pellets are detected.

More specifically, this method can be referred to as deconvolution signal analysis to characterize different variables of interest monitored with the system. By correlating a variable to a range of frequencies within the electronic signal generated by the photo detector, it is possible to isolate its corresponding light attenuation values.

Since a frequency is the number of occurrences of a repeating event per unit time, we can classify variables as lower or higher frequency parameters. The case of discriminating attenuation values specific to fish swimming in an aquaculture cage and attenuation values specific to feed pellets being thrown in the aquaculture cage to feed the fish is one example where this can be done. Feed pellets sink down the cage at a constant rate in the order of 4 inches (~10 cm) per second depending on the type of feed, and therefore stay in the field of view of the sensor for a considerable amount of time. Salmon swim at an average speed in the order of 20 inches (~50 cm) per second and are thus subject to rapid changes in direction. Subsequently, with XpertSea system, feed pellets sinking down the cage are recorded at a lower frequency than fish swimming randomly in the water.

Figure 4A:
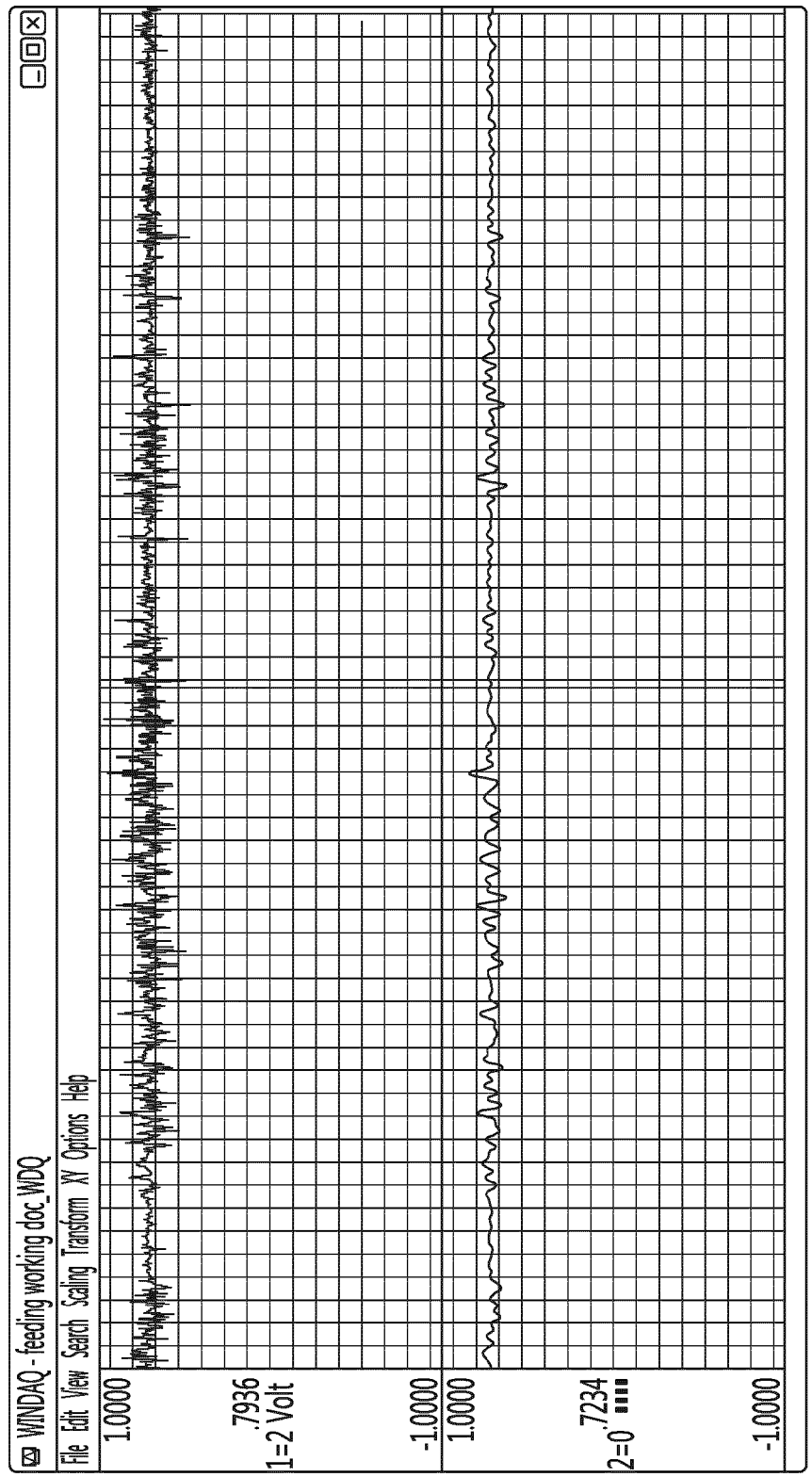
FIGS. 4A and 4B are graphs showing the isolation of frequencies attributable to a variable of interest.
Figure 4B:
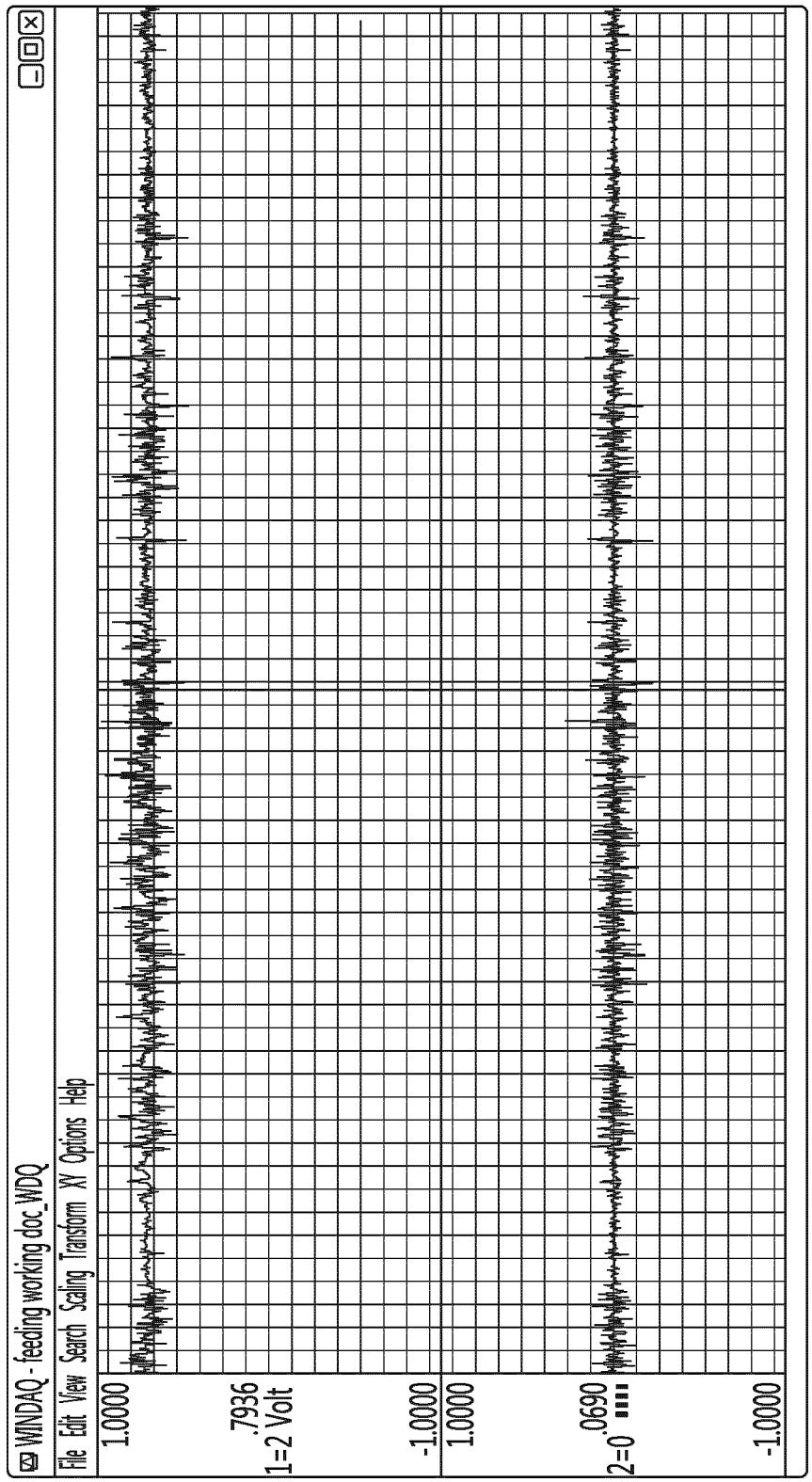

FIGS. 4A and 4B illustrate a specific example where this method was used to isolate the attenuation values specific to the feed pellets and the fish using the signal deconvolution method. The signal on top of FIGS. 4A and 4B is the raw waveform recorded by the system while fish were being fed in an aquaculture cage. A Discrete Fourier Transform was performed on the raw waveform to characterize the amplitude of each frequencies present within the signal. In FIG. 4A, a low pass filter was applied to the transform (illustrated as the bottom signal of FIG. 4A) to remove frequencies higher than 2 Hz. The resulting values expressed in the middle row of FIG. 1 are specific to the light attenuation caused by the feed pellets.

The same process was applied to FIG. 4B, however instead of a low pass filter, a high pass filter was applied to erase all frequencies lower than 2 Hz and only keep higher frequencies between 2 Hz and 10 Hz. The values illustrated in the middle row of FIG. 4B are thus specific to the light attenuation caused by the fish swimming in the water. The same process could be applied once again to the higher frequencies to discriminate between the variance induced by the fish and the signal fluctuation caused by a high frequency electrical noise.

A similar process can be used to identify a level of activity of the fish (which can be correlated to health level), identifying a predator in the cage, determining the size distribution of the population, etc.

Other useful information can be obtained by tracking the intensity variations over a period of time. For instance, reliable data that can be correlated to various variables of interests such as fish or shellfish counts and size, involves collecting a large amount of values. In fact, since marine organisms swim around in the water body, many measurements can be required to obtain a truly representative sampling of the specimens. For example, fish tend to overlap and form clusters. When the final ratios or light intensity values are not based on single measurements but rather on the average of hundreds of data collected over a fix interval of time, the variations among the individual data collected during that interval of time can provide information about the behavior of the marine organisms in the water. If data are recorded every second for 5 minutes, 300 individual values are generated. If the fish are not active during this five minute interval, the variation within the 300 values is minimal. On the other hand, if the fish are feeding, their random motion generates high variations in the data set. In the end, the mean value of the two data sets is similar; however their standard deviation value differs greatly. Using this technique, one can correlate the standard deviation value of a data set to the level of activity of the marine organism population.

To obtain a better accuracy and/or versatility, the readings can be triggered by light emitted within a spectrum which can be centered on one or more predetermined wavelengths, rather than using simply direct sunlight. For instance, direct sunlight may be unavailable on a very cloudy day where readings are desired. In embodiments which use emitted light and which are subjected to ambient light, it can be useful, and perhaps even essential, to use an ambient light detector to obtain an indication of the ambient light contribution to the detected intensity, and to allow correcting the detected intensity accordingly.

In embodiments where direct sunlight is used as the light source, the ambient light intensity is one variable which can be taken into consideration with an appropriate calibration algorithm.

Generally, the larger the open ocean cage is, the greater the amount of detectors and optionally emitters are required to obtain satisfactory accuracy representative of the entire open ocean cage.

In a specific embodiment, the detectors are connected individually to the opto-electronic unit using a marine grade wire to allow for strategic positioning throughout the cage. Also, using lasers as the lighting source may be an issue due to the limited power availability at the location of the cage. The alternative is using LED lamps that emit at specific spectral bands (such as green and red for instance). The LED lamps can be durable, low cost and energy efficient. Using LED lamps, the entire system (light sources, detectors and datalogger) can be powered using a 12 VDC battery which is recharged using a waterproof solar panel. One strategy to reduce energy consumption is to take readings only at certain periods in time, such as each hour for instance, which can also prevent the attraction of photo tactic parasites on any emitters. A power supply and electronic unit can be secured in a rugged waterproof casing which floats on a raft attached to a buoy. It can be advantageous to provide an open sea system which collects a relatively small volume of the data which be transferred wirelessly. Cages can be spherical or barrel shaped for instance. If used, light sources can be strategically positioned around the cage structure. In embodiments where the diameter of the cage is very long (such as more than 10 meters for instance) installing the light sources on a center axle of the cage can be preferable. The detectors can be made of one, two or more detection units which are enclosed in waterproof casings having a glass or acrylic front window which allows energy from the light to reach the active area of the photodiodes. A CCD lens, a photodiode, and an electrical circuit board (for signal amplification and noise reduction) can be part of the detection unit. A reflective panel can also be installed to collect light more effectively. Laser line filters or broad band filters can be added if LEDs of different spectral bands are used. A water proof connector can allows the power and signal wires to connect to the electrical circuit board to the opto-electrical unit. Light sources can be turned on simultaneously or individually to measure transmittance and back-scattering of light. The number of light sources can range from one to ten or more depending on the size of the cage and the emitting power of the lights. Light sources can be installed around the cage structure on a central hub. Using the data generated by different combinations of light sources and detectors, along with statistical parameters, reference values and calibration of external variables, several variables of interests can be measured.

For instance, some detectors can be placed at 0 degrees and 180 degrees with respect to the light sources. This makes possible the monitoring of the light backscattered by the fish (0 degrees) and the light transmitted through the fish population (180 degrees). As the number of fish in the cage increases, the amount of backscattered light to detector at 0 degrees also increases but the quantity of light that makes it to detector at 180 degrees decreases. Using the ratio of backscatter to transmitted light, one can approximate the quantity of fish in the cage. However, this ratio of backscatter to transmitted light will also be affected by the size of the fish. Therefore, in order to develop an accurate algorithm for fish quantity, the size distribution of the fish population needs to be known.

Another example is using the forward scattering phase function (FSPF) of particles to obtain information about the size of the particles in the water. This can be achieved by placing detectors at different viewing angles all around the cage (0, 45, 90, 135, and 180 degrees). Without any fish in the cage, a constant light intensity is recorded by the sensors as a function of their distance and angle with respect to the light sources. However, as fish are introduced in the cage, scattering of the fish will happen as a function of the size of the fish. When fish are small, light will be scattered uniformly around the cage. However, as the fish increase in size, the larger specimens will generate more forward scattering to the detectors located at the opposite of the light source. Therefore, one can determine the size distribution of the fish population within the cage by looking at the ratio of light intensity recorded by the detectors at different angles with respect to the light source.

In still another example, the infection of fish populations in cages by parasite or a viral disease can be monitored using the system if the infection induces changes in the physical properties of the fish surface such as changes in pigmentation or texture. For example, in ocean cage farming settings, sea lice can be a severe issue. When the sea lice copepods find a fish host, they develop into adult parasites that attach the fish skin. If sea lice are infecting the fish population within the cage, the intensity of green backscattered light will decrease since the pigmentation of the sea lice organisms absorbs the green spectrum of light. However, the pigment characteristic of the sea lice tissues does not absorb as much light in the red spectrum. Therefore, an unusual decrease in the green to red backscattered light intensity ratio can be correlated to a change in fish skin pigmentation caused by sea lice infection.

Also, still using two wavelengths of emitted light, it is possible to determine the turbidity of the water using the ratio of green to red light measured by the detector at 180 degrees. In fact, the light reaching the detector at 180 degrees made it through the fish population mainly without being scattered by the fish. Therefore, the only attenuation experienced by this light comes from the water and the small suspended particles. Since green light is more absorbed by suspended particles than red light, a high ratio of green to red transmitted light indicates a low concentration of the suspended particle. On the other hand, a low ratio of green to infrared transmitted light indicates a high concentration of suspended sediments. This high concentration suspended particles can be correlated to events such as algal or parasite blooms or pollution events.

As can be understood now, the examples described above and illustrated are intended to be exemplary only. The scope is indicated by the appended claims.

What is claimed is:

1. A photo-coupled data acquisition system comprising a container having a contour wall extending upwardly from a closed bottom, for containing a sample therein, a light emitter operable to emit diffused light into the container at an initial intensity, a photodetector operable to detect a reflected intensity of the diffused light reflected by at least one of the sample and the container across the sample, and a structure connected to the contour wall and holding the light emitter and the photodetector at a predetermined height above the bottom of the container and in an orientation facing inside the container, the contour wall and the bottom being part of a bucket having an open upper end, the structure being formed by a lid securable to the open upper end of the bucket, and to which both the light emitter and the photodetector are mounted, the contour wall, bottom, and lid being opaque to prevent intrusion of ambient light inside the container, and the inner face of the contour wall and bottom being reflective to the diffused light, wherein during operation of the system, the initial intensity is attenuated by the sample in a manner that the reflected intensity can be correlated to an information value concerning a variable of interest of the sample.

2. The photo-coupled data acquisition system of claim 1 further comprising, a memory to store calibration data, and a processor operable to correlate the reflected intensity to the information value using the calibration data.

3. The photo-coupled data acquisition system of claim 2 further comprising a visual indicator; wherein the sample has a plurality of organisms in a liquid medium, and the processor is operable to display a quantity of organisms on said visual indicator, said quantity of organisms being determined based on said comparison.

4. The photo-coupled data acquisition system of claim 2 further comprising a data storage port accessible by the processor for storing reflected intensity data.

5. The photo-coupled data acquisition system of claim 1 wherein the container forms a closed sample volume shielded from external light.

6. The photo-coupled data acquisition system of claim 1 wherein the contour wall has a cylindrical shape extending upwardly from the bottom.

7. The photo-coupled data acquisition system of claim 1 wherein the photodetector is a first photodetector operating within a first wavelength band, further comprising a second photodetector operating within a second wavelength band distinct from the first wavelength band; wherein the processor is operable to obtain independent information values concerning different values of interest of the sample using the two wavelength bands.

8. The photo-coupled data acquisition system of claim 1 wherein the light emitter is a first light emitter operating within the first wavelength band, further comprising a second light emitter operating within the second wavelength band.

9. The photo-coupled data acquisition system of claim 1 wherein the contour wall has a horizontal marking corresponding to a predetermined calibration volume of the liquid medium.

10. A photo-coupled data acquisition system comprising a container having a contour wall extending upwardly from a closed bottom, for containing a sample therein, the sample having given volume of liquid medium, the sample having a surface which reaches a sample level in the container, a light emitter operable to emit diffused light and to diverge the diffused light into the container at an initial intensity, a photodetector operable to detect a reflected intensity of the diffused light reflected by at least one of the sample and the container across the sample, and a structure connected to the contour wall and holding the light emitter and the photodetector at a predetermined height above the given level and in an orientation facing inside the container, wherein during operation of the system, a spacing is present between the light emitter and the given level of the sample, the spacing allowing divergence of the diffused light onto the surface of the sample at the sample level and wherein the initial intensity is attenuated by the sample in a manner that the reflected intensity can be correlated to an information value concerning a variable of interest of the sample.

11. A photo-coupled data acquisition system comprising; a container having a contour wall extending upwardly from a closed bottom for containing a sample therein, the sample having a plurality of organisms in a liquid medium; a light emitter operable to emit diffused light into the container at an initial intensity; a photodetector operable to detect a reflected intensity of the diffused light reflected by at least one of the sample and the container across the sample; a structure connected to the contour wall and holding the light emitter and the photodetector at a predetermined height above the bottom of the container and in an orientation facing inside the container, wherein during operation of the system, the initial intensity is attenuated by the sample in a manner that the reflected intensity can be correlated to an information value concerning a quantity of organisms of the sample; a memory to store calibration data; a processor operable to correlate the reflected intensity to the information value using the calibration data; and a visual indicator; wherein the processor is operable to display a quantity of organisms on said visual indicator, said quantity of organisms being determined based on said correlation.

* * * * *